United States Patent [19]
Lynn

[11] Patent Number: 5,785,643
[45] Date of Patent: Jul. 28, 1998

[54] LAPAROSCOPIC SCOPE MANIPULATOR

[75] Inventor: Jim Lynn, 109 W. Paseo de Cristobal, San Clemente, Calif. 92672

[73] Assignee: Jim Lynn, San Clemente, Calif.

[21] Appl. No.: 507,771

[22] Filed: Jul. 26, 1995

[51] Int. Cl.$^6$ ................................................ A61B 1/00
[52] U.S. Cl. ........................................ 600/125; 600/121
[58] Field of Search ........................ 128/849, 851, 128/852, 856; 600/121–125, 227, 229, 230

[56] References Cited

U.S. PATENT DOCUMENTS

| | | | |
|---|---|---|---|
| 3,858,578 | 1/1975 | Milo | 600/229 |
| 4,522,196 | 6/1985 | Cunningham et al. | 600/122 |
| 4,573,452 | 3/1986 | Greenberg | 600/229 |
| 4,817,592 | 4/1989 | Auchinleck et al. | 128/856 |
| 4,914,521 | 4/1990 | Adair | 600/122 X |
| 5,105,800 | 4/1992 | Takahashi et al. | 600/121 |
| 5,184,601 | 2/1993 | Putnam | 600/122 |
| 5,251,613 | 10/1993 | Adair | 600/125 |
| 5,284,130 | 2/1994 | Ratliff . | |
| 5,441,042 | 8/1995 | Putnam | 600/227 |
| 5,447,149 | 9/1995 | Kikawada et al. | 600/229 |
| 5,498,230 | 3/1996 | Adair | 600/124 X |

FOREIGN PATENT DOCUMENTS

9220295  11/1992  WIPO .

OTHER PUBLICATIONS

Bookler™ Laparoscopic Holding/Positioning Devices—Mediflex (1993) (1 page).
AESOP—Automated Endoscopic System for Optimal Positioning (1993) (2 pages).
Omni–Tract Accessories Specifically for the Omni–Lapo–Tract Support Systems (Apr. 93) (1 page).
The Omni–LapoTract™ Support System from Omni–Tract (1993) (1 page).
Cysto/Splash Drape (1993) (1 page).
Laparoscopic Devices & Instruments—Mediflex (No Date) (1 page).
The Mediflex™ Universal Holding/Positioning System (1992)—Mediflex (1 page).
The Mediflex™ Universal Holding/Positioning System (Mobile Flexible Positioning Arms with Adjustable Rigidity ... —Mediflex (1992) (1 page).
Bookler™ Laparoscopic Holding/Positioning Devices—Mediflex (1992) (1 page).
Mediflex Surgical Products—Mar. 1994 (1 page).

*Primary Examiner*—Jeffrey A. Smith
*Attorney, Agent, or Firm*—Cislo & Thomas

[57] ABSTRACT

A positioner or manipulator for an endoscope, laparoscope, or other surgical instrument, includes a flexible arm having a base attached to an operating table. A drape joint at the upper end of the arm has a tubular sterile drape which is pulled back over the arm, to provide a sterile field around the arm. A scope ring adapted to hold a scope or other instrument attaches to the drape joint. The attachments between the scope ring, drape joint and arm are preferably made with quick release fittings. The need to sterilize the arm is removed, decreases hospital operation costs, and increasing the level of sterility.

13 Claims, 3 Drawing Sheets

LAPAROSCOPIC SCOPE MANIPULATOR

BACKGROUND OF THE INVENTION

The field of the invention is manipulators and positioners for surgical instruments, including laparoscopes.

Laparoscopic surgery is generally performed by introducing surgical instruments to a site within a patient, through small incisions through the skin and overlying tissues. Cutting, stapling, and other laparoscopic instruments are manipulated within the body cavity through a cannula/trocar, which creates and maintains the opening into the surgical site. Insufflation may be used to separate internal organs and provide room for viewing and instrument manipulation. Unlike conventional surgery, the surgical site cannot be viewed directly. Visualization is provided by introducing lights and a laparoscope to the surgical site, in the same manner as the other surgical instruments. The image from the surgical site is transmitted from the laparoscope and displayed on a monitor. The laparoscope must be held in an appropriate position to achieve a viewing angle of the surgical site sufficient for the surgeon to operate. Typically, an assisting surgeon or other medical personnel holds and manipulates the laparoscope for the operating surgeon.

However, to reduce the cost of medical care and treatment, eliminating the need for a second person to hold and manipulate the laparoscope, would be advantageous. To meet this need, various holding/positioning devices for laparoscopes have been proposed. For example, Ratliff, U.S. Pat. No. 5,284,130 describes a surgical instrument positioning and securing apparatus for use with endoscopic surgical techniques. Various other generally simpler laparoscope instrument holders have also been used. These holders typically have ball and socket clamping features, to allow the segmented holder/positioner to be freely moved into position and then locked in place, to hold an instrument at a fixed location. While these known devices may adequately hold or position scopes or instruments, they can be difficult to clean and sterilize, especially devices having exposed interconnected segments. As the holder/positioner may be brought into the sterile field around the surgical site, sterility of the holder, although difficult to achieve, is important.

Accordingly, it is an object of the invention to provide a surgical instrument or scope positioner/holder which avoids the cleaning and sterilizing difficulties associated with other positioners and holders, thereby reducing hospital operating expenses, improving on the level of sterility of positioner/holders, and decreasing the turn around time required to prepare and reuse a positioner/holder.

SUMMARY OF THE INVENTION

To these ends, a positioner/holder for a surgical instrument or scope, preferably includes a flexible arm having a lower end attachable to an operating room table. A drape joint is preferably attached to the upper end of the flexible arm with a quick release fitting. The drape joint includes a tubular drape which is pulled back and down over the flexible arm, to provide a sterile barrier. An instrument holder, or scope ring is attached to the drape joint, preferably with another quick release fitting. Accordingly, the arm is uniformly shielded by the drape, which is provided as a sterile and disposable component. The arm itself therefore need not be sterilized between procedures.

Accordingly, it is an object of the invention to provide an improved surgical instrument and scope holder/positioner.

BRIEF DESCRIPTION OF THE DRAWINGS

In the drawings, wherein in similar reference characters denote similar elements throughout the several view.

DETAILED DESCRIPTION OF THE DRAWINGS

Figure 1:
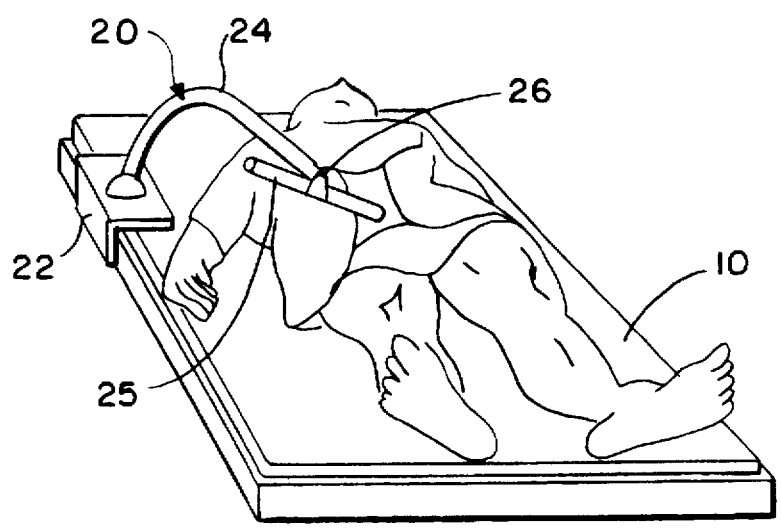
FIG. 1 is a perspective view of the present laparoscopic scope manipulator.
Figure 2:
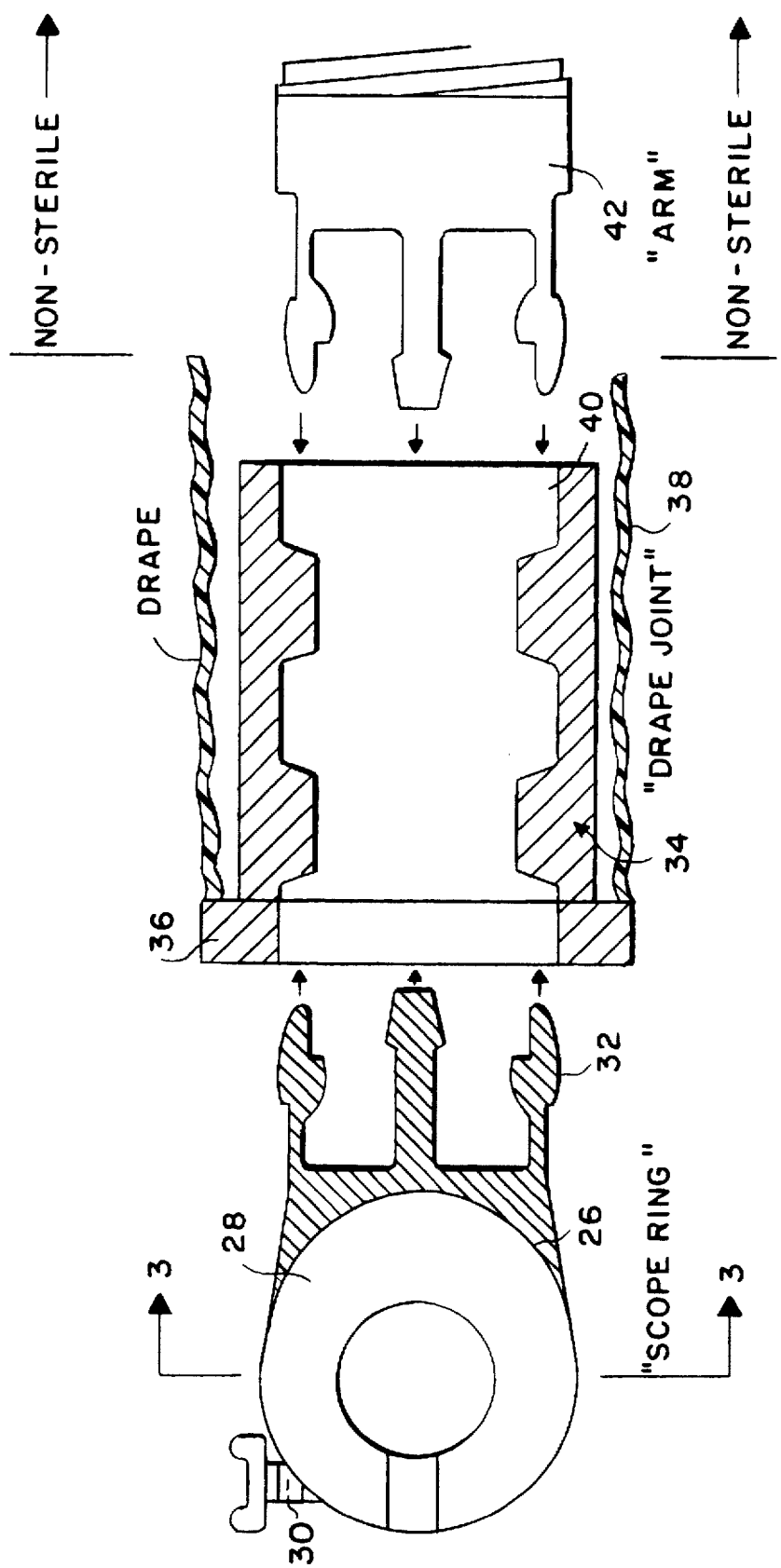
FIG. 2 is an exploded partial side elevation view, in part section, thereof.
Figure 3:
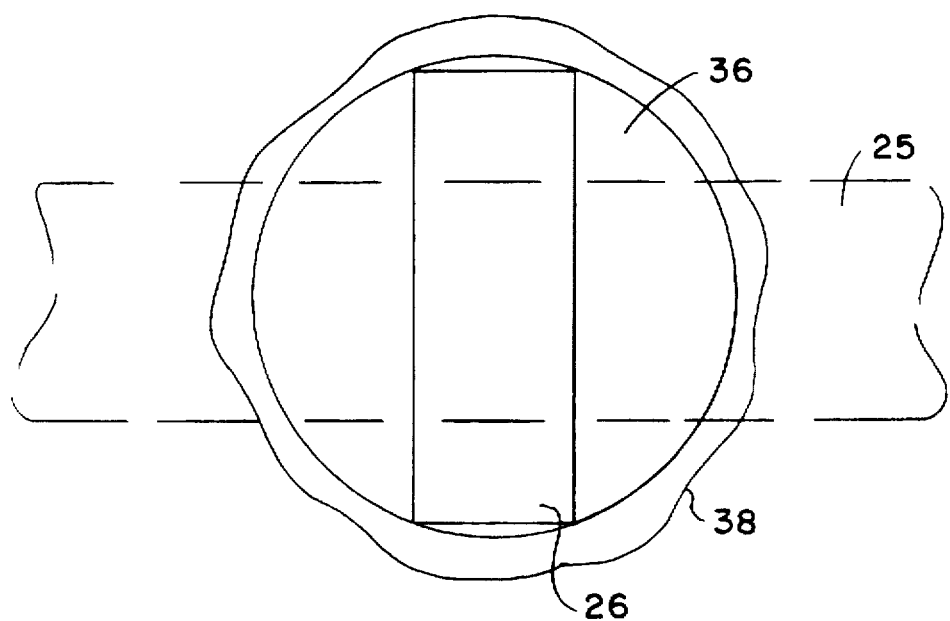
FIG. 3 is a front section view thereof.

Turning to the drawings, as in FIG. 1, the present manipulator/positioner 20 has a base 22 attachable to an operating table 10. A lower end of an arm assembly 24 is attached to the base 22. The upper end of the arm assembly 24 has a scope ring 26 for holding a scope 25, or other instrument. Turning to FIGS. 2 and 3, an arm fitting 42 is attached at the upper end of the arm assembly 24. A drape joint 34 has a drape 38 permanently attached and sealed onto a flange 36. A drape joint fitting 40 is attached to the flange 36 and mates with the arm fitting 42. The fittings 40 and 42 are preferably quick release.

The scope ring 26 has a clamp 28 and fastener 30 for clamping around a scope 25. The scope ring 26 has a fitting 32 engageable into a joint quick release fitting on the front end of the fitting 40 of the drape joint 34.

Figure 4:
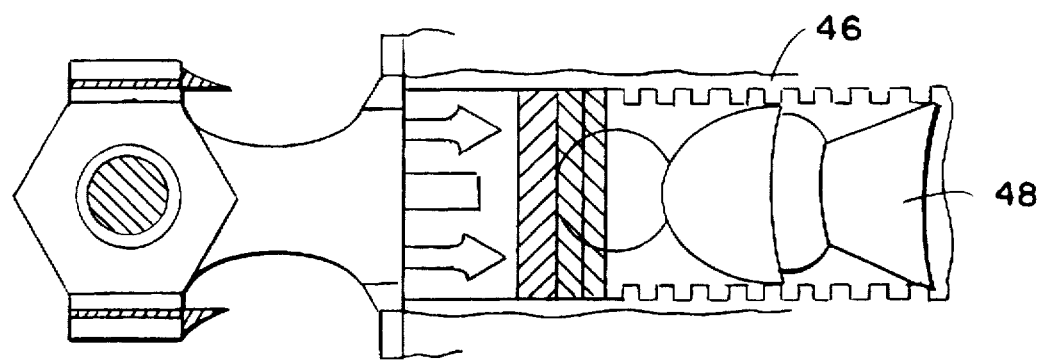
FIG. 4 is a side elevation view, in part section, illustrating a preferred embodiment.

As shown in FIG. 4, the arm assembly 24 may advantageously be formed from a series of friction locked interconnected ball and socket segments 48 which have sufficient internal friction to support an instrument at the end of the arm, yet still allow the arm to be moved and shaped into a desired position, without undue force. A flexible tube 46 is preferably provided over the segments 48.

In use, the drape joint 34 and the scope ring 26 are preferably provided in a sterile package as disposable items, whereas the arm is advantageously reused. The sterile drape joint is removed from its package, snapped onto the arm fitting 42 at the front end of the arm assembly 24, and the rolled or bunched up cylindrical drape 38 is unrolled or unfurled down over the length of the arm assembly 24, preferably to the base 22. The drape 38 provides a sterile barrier between the sterile surgical field and the arm assembly 24. The sterile, disposable scope ring 26 is clamped onto a scope or other instrument, and snapped into the front end of the drape joint 34. The arm assembly 24 itself may be of conventional design, and allows the scope or instrument to be manipulated or positioned in the traditional way, but with the drape 38 over the arm providing a sterile barrier.

After the operation is completed, the scope ring 26 is detached and separated from the drape joint 34. The scope ring is then detached from the instrument and discarded. The drape joint 34 is similarly separated from the arm assembly 24 and discarded. The arm assembly 24 is prepared for the next operation by installing a new drape joint 34. In this manner, the relatively difficult procedure of sterilizing the arm assembly 24 is no longer required. Thus, the invention provides the advantages of a positioner/manipulator achieving a high degree of sterility, reduced hospital operation costs as sterilizing the arm is unnecessary, and faster turn around time for reuse of the arm as replacement of the drape joint 34 can be quickly and easily achieved, in contrast to sterilization of the arm.

Various modifications may, of course, be made without departing from the spirit and scope of the invention.

I claim:

1. A drape assembly for attaching a flexible arm to an instrument holder comprising:

a drape joint releasably attachable to the arm; and a drape unitary to said drape joint;

wherein said drape assembly being discardable after use, and the flexible arm being attachable to the instrument holder only when the drape is present.

2. The drape assembly of claim 1 wherein said drape joint having a projecting flange guarding against detachment of said drape from said drape joint.

3. The drape assembly of claim 2 wherein said drape being sized to be extendable from said drape joint along the flexible arm away from the instrument holder.

4. sterile drape system for attaching a postionable arm having a quick-release fitting to a scope ring for holding an endoscope or laparoscope and having a quick-release fitting comprising:

a drape joint having an arm fitting engageable onto the arm quick-release fitting, and a joint fitting engageable onto the scope ring quick-release fitting; and said drape joint having a unitary drape;

wherein said drape assembly being discardable after use, and the positionable arm being attachable to the scope ring only when the drape is present.

5. The sterile drape system of claim 4 wherein said drape joint having a circumferential flange to which the drape is attached, the flange to guard against detachment of said drape from said drape joint.

6. The sterile drape system of claim 5 wherein said drape being sized in diameter and length to be extendable from said circumferential flange a substantial distance along the positionable arm away from the scope ring.

7. A surgical instrument positioner comprising:

a flexible arm;

a drape joint releasably attached to the arm;

a drape unitary to said drape joint; and an instrument holder releasably attached to said drape joint;

wherein said drape assembly being discardable after use, and the flexible arm being attachable to the instrument holder only when the drape is present.

8. The surgical positioner of claim 7 wherein said drape joint having a flange guarding against detachment of said drape from said drape joint.

9. The surgical drape positioner of claim 8 wherein said drape being sized to be extendable from said drape joint along the flexible arm away from the instrument holder.

10. An endoscope/laparoscope positioner comprising:

a positionable arm having an arm quick-release fitting;

a drape joint having an arm fitting releasably engaged onto said arm quick-release fitting, a joint quick-release fitting, and a unitary drape; and a scope ring for holding an endoscope or laparoscope and having a ring quick-release fitting releaseably engaged onto the joint quick-release fitting;

wherein said drape assembly being discardable after use, and the positionable arm being attachable to the scope ring only when the drape is present.

11. The endoscope/laparoscope positioner of claim 10 wherein said drape joint having a circumferential flange to guard against detachment of said drape from said drape joint.

12. The endoscope/laparoscope positioner of claim 11 wherein said drape being sized in diameter and length to be extendable from said circumferential flange a substantial distance along the positionable arm away from the scope ring.

13. A surgical instrument positioner comprising:

a flexible arm having a first end and a second end;

a drape joint releaseably attached to the first end of the arm;

a drape attached to the drape joint; and an instrument holder releasably attached to the drape joint;

wherein said drape joint must be present to connect the flexible arm to the instrument holder.

* * * * *